(12) United States Patent
Kamiya et al.

(10) Patent No.: US 8,178,105 B2
(45) Date of Patent: May 15, 2012

(54) **COMPOSITION CONTAINING *AGARICUS BLAZEI* MURILL**

(75) Inventors: Toshikazu Kamiya, Tsukuba (JP); Shun Kayahashi, Tokyo (JP); Akio Shirai, Tokyo (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 325 days.

(21) Appl. No.: 12/519,190

(22) PCT Filed: Dec. 14, 2007

(86) PCT No.: PCT/JP2007/074096
§ 371 (c)(1),
(2), (4) Date: Jun. 15, 2009

(87) PCT Pub. No.: WO2008/072725
PCT Pub. Date: Jun. 19, 2008

(65) Prior Publication Data
US 2010/0040715 A1    Feb. 18, 2010

(30) Foreign Application Priority Data
Dec. 15, 2006    (JP) .................. 2006-338689

(51) Int. Cl.
*A61K 36/06*    (2006.01)

(52) U.S. Cl. ................................. 424/195.15

(58) Field of Classification Search ........................ None
See application file for complete search history.

(56) References Cited

U.S. PATENT DOCUMENTS 6,143,786 A * 11/2000 Gohman et al. .............. 514/565

FOREIGN PATENT DOCUMENTS

| JP | 04-282313 A | 10/1992 |
| JP | 10-316589 A | 12/1998 |
| JP | 2004-357507 A | 12/2004 |

OTHER PUBLICATIONS

DW ACC 1999-261446, Mar. 1999, Derwent or JP11, Sadoyama.*
DW ACC 2005-242020, Mar. 2005, Derwent or WO20, Koide.*
Eguchi et al., *Journal of Traditional Medicines*, 16(5): 201-207 (1999).
Elvehjem, *Federation Proceedings*, 15: 965-970 (1956).
Iwasa et al., *J. Natl. Def. Med. Coll.*, 7(1): 8-15 (1982).
Kawaura et al., *Journal of New Remedies & Clinics*, 26(10): 1877-1880 (1977).
Kojima et al., *Exp. Animals*, 22(3): 237-242 (1973).
Tachibana et al., *Journal of Parenteral and Enteral Nutrition*, 9(4): 428-434 (1985).

* cited by examiner

*Primary Examiner* — Christopher R Tate
*Assistant Examiner* — Randall Winston
(74) *Attorney, Agent, or Firm* — Leydig, Voit & Mayer, Ltd.

(57) ABSTRACT

The invention provides a composition containing a fruit body of *Agaricus blazei* murill or an extract of the fruit body, and an amino acid constituting the ornithine cycle or a salt thereof, wherein the pharmacological activities of the fruit body of *Agaricus blazei* murill or the extract of the fruit body and the amino acid constituting the ornithine cycle or the salt thereof are increased synergistically. Such a composition can contain a fruit body of *Agaricus blazei* murill or an extract of the fruit body, and an amino acid constituting the ornithine cycle or a salt thereof in 10-100 parts by weight per 1 part by weight of the fruit body or the extract.

6 Claims, No Drawings

COMPOSITION CONTAINING *AGARICUS BLAZEI* MURILL

TECHNICAL FIELD

The present invention relates to a composition comprising a fruit body of *Agaricus blazei* Murill or an extract of the fruit body, and an amino acid constituting the ornithine cycle or a salt thereof.

BACKGROUND ART

*Agaricus blazei* Murill is originated from Piedate, a local area in Brasil, and is one kind of the mushrooms eaten in the area for a long time. In recent years, it has also been grown in Japan, and used as raw food and for medicinal purposes. Known efficacy of *Agaricus blazei* Murill includes enhancement and improvement of the liver, heart, stomach, intestines and the like, stabilization of blood pressure and blood glucose level, recovery of lumbago or neck stiffness, prevention of aging, improvement of immunity and the like. The efficacy attracting highest attention is an antitumor action (see patent document 1).

Researches utilizing the concept of amino acid imbalance proposed by Elvehjem in 1956 are ongoing on suppression of tumor growth by inhibiting protein synthesis in cancer tissues (see non-patent document 1). To be precise, attempts have been made to prevent growth of cancer cells by artificially creating a deficiency or excess state of a particular amino acid, and as one of such studies, amino acid imbalance preparations containing arginine in excess have been reported (see non-patent documents 2-4). It has also been reported that oral administration of arginine to Sarcoma-180 transplanted mouse affords marked antitumor effect and life extension (see non-patent document 5). Moreover, it is known that arginine, ornithine and citrulline constitute an in vivo ornithine cycle, and ornithine and citrulline are converted to arginine in the cycle.

In addition, a supplement for pet containing an extract of Agaricus or agaricus dried powder, and an amino acid is known (see patent document 2).

patent document 1: JP-A-10-316589
patent document 2: JP-A-2004-357507
non-patent document 1: "Fed. Proc.", 1956, vol. 15, p 965
non-patent document 2: "Journal of New Remedies & Clinics", 1977, vol. 26, No. 10, p 1877
non-patent document 3: "J Natl Def Med Coll", 1982, vol. 7, No. 1, p 8
non-patent document 4: "J. Parent. Enter. Nutr.", 1985, vol. 9, No. 4, p 428
non-patent document 5: "Exp. Animals", 1973, vol. 22, No. 3, p 237-242

DISCLOSURE OF THE INVENTION

Problems to be Solved by the Invention

An object of the present invention is to provide a composition comprising a fruit body of *Agaricus blazei* Murill or an extract of the fruit body, and an amino acid constituting the ornithine cycle or a salt thereof, which affords synergistically enhanced pharmacological activity of each of the fruit body of *Agaricus blazei* Murill, an extract of the fruit body, and an amino acid constituting the ornithine cycle and a salt thereof.

Means of Solving the Problems

The present invention relates to the following (1) to (8).

(1) A composition comprising a fruit body of *Agaricus blazei* Murill or an extract of the fruit body, and an amino acid constituting the ornithine cycle or a salt thereof in 10-100 parts by weight per 1 part by weight of the fruit body or the extract.

(2) A composition comprising a fruit body of *Agaricus blazei* Murill or an extract of the fruit body, and an amino acid constituting the ornithine cycle or a salt thereof in 20-80 parts by weight per 1 part by weight of the fruit body or the extract.

(3) A composition comprising a fruit body of *Agaricus blazei* Murill or an extract of the fruit body, and an amino acid constituting the ornithine cycle or a salt thereof in 30-60 parts by weight per 1 part by weight of the fruit body or the extract.

(4) The composition of any one of the above-mentioned (1)-(3), wherein the content of the fruit body of *Agaricus blazei* Murill or an extract of the fruit body, and the amino acid constituting the ornithine cycle or a salt thereof is 0.1-100 wt %.

(5) The composition of any one of the above-mentioned (1)-(3), wherein the content of the fruit body of *Agaricus blazei* Murill or an extract of the fruit body, and the amino acid constituting the ornithine cycle or a salt thereof is 0.5-80 wt %.

(6) The composition of any one of the above-mentioned (1)-(3), wherein the content of the fruit body of *Agaricus blazei* Murill or an extract of the fruit body, and the amino acid constituting the ornithine cycle or a salt thereof is 1.0-70 wt %.

(7) The composition of any one of the above-mentioned (1)-(6), wherein the amino acid constituting the ornithine cycle is arginine, ornithine or citrulline.

(8) The composition of the above-mentioned (7), wherein the amino acid constituting the ornithine cycle is arginine.

Effect of the Invention

According to the present invention, a composition comprising a fruit body of *Agaricus blazei* Murill or an extract of the fruit body, and an amino acid constituting the ornithine cycle or a salt thereof, and having a superior pharmacological activity can be provided.

BEST MODE FOR CARRYING OUT THE INVENTION

Examples of the fruit body of *Agaricus blazei* Murill in the present invention include a wild fruit body and a fruit body obtained by culture, which may be directly obtained or subjected to a physical, chemical or biological treatment to give various treatment products and the like.

Examples of the physical or chemical treatment method include drying treatments such as solar drying, air drying, freeze-drying and the like, milling treatments using blender, homogenizer, ball mill and the like, and the like, and examples of the physically or chemically treated product include dried product, freeze-dried product, milled product and the like. Examples of the biological treatment method include fermentation method and the like, and examples of the biologically treated product include fermented products. Among the various types of treatment products, dried products and freeze-dried products are preferable.

Examples of the fruit body extract include extracts obtained from the aforementioned fruit body by various extraction methods. Examples of the extraction method include various solvent extraction, supercritical fluid extraction and the like. The extract may be treated by various solid-liquid separation methods such as sedimentation separation, cake filtration, clarification filtration, centrifugal filtration, centrifugation sedimentation, compression separation, filter press and the like, various concentration methods, various drying methods, preparation formulation methods such as granulation, powderization and the like, various purification methods and the like.

Examples of the purification method include dialysis, solvent fractionation, column chromatography, recrystallization and the like. As the column chromatography, column chromatographys using various carriers such as TOYOPEARL HW40C (manufactured by Tosoh Corporation), Diaion HP-20 (manufactured by Mitsubishi Chemical Corporation), Sephadex LH-20 (manufactured by Pharmacia Biotech) and the like are preferable.

Examples of the concentration and drying methods include drying methods such as freeze-drying, natural air drying, hot air drying, ventilation drying, fan drying, spray drying, drying under reduced pressure, solar drying, vacuum drying, fluid bed drying, foam-mat drying, film drying such as drum dryer and the like, ultrasonication drying, electromagnetic wave drying and the like, with preference given to freeze-drying method.

For extraction and treatment of an extract, for example, an antioxidant, a preservative and the like may also be added.

As the solvent to be used for solvent extraction, any solvent may be used as long as it can extract a pharmacologically active ingredient contained in a fruit body of *Agaricus blazei* Murill. Examples thereof include aqueous media such as water, distilled water, deionized water, aqueous inorganic salt solution, buffer and the like, monovalent alcohols such as methanol, ethanol, propanol, butanol and the like, polyvalent alcohols such as propylene glycol, glycerol and the like, organic solvents such as hexane, toluene, petroleum ether, benzene, ethyl acetate, chloroform, dichloromethane, 1,1,2-trichloroethene, dimethyl sulfoxide, acetone and the like, and the like.

Examples of the buffer include phosphate buffer, citrate buffer and the like. Examples of the inorganic salt of the aqueous inorganic salt solution include sodium chloride, potassium chloride, calcium chloride and the like.

These solvents may be used alone or in a mixture of plural solvents.

Extraction is performed using, for example, 0.1 part by weight—10000 parts by weight, preferably 1 part by weight—100 parts by weight, of a solvent per 1 part by weight of the fruit body. While the extraction temperature is not particularly limited, it is preferably 0° C.-100° C., more preferably 20° C.-90° C. While the extraction time is not particularly limited, 1 min-1 week is preferable, and 30 min-1 day is more preferable.

While the aqueous medium is not particularly limited, water, pure water and deionized water are preferable. While the extraction temperature of extraction with aqueous medium, alcohol or water-containing alcohol is not particularly limited, 0° C.-100° C. is preferable, and 20° C.-90° C. is more preferable. While the extraction time is not particularly limited, 1 min-1 week is preferable, and 30 min-1 day is more preferable. As the fruit body, dry-treated one is preferably used.

While the instrument to be used for the extraction is not particularly limited, container, stirring machine, refluxing condenser, Soxhlet extractor, homogenizer, shaking machine, ultrasonication generator and the like, which have been engineered for efficient extraction, can be mentioned.

Examples of the amino acid constituting the ornithine cycle to be used in the present invention include arginine, ornithine, citrulline and the like, with preference given to arginine. The above-mentioned amino acid may be used alone or in a mixture of two or more kinds thereof. The above-mentioned amino acids to be used may be each an L-form, a D-form, or a mixture of an L-form and a D-form, with preference given to an L-form.

Examples of the salt of the amino acid constituting the ornithine cycle include acid addition salt, metal salt, ammonium salt, organic amine addition salt, amino acid addition salt and the like.

Examples of the acid addition salt include inorganic acid salts such as hydrochloride, sulfate, nitrate, phosphate and the like, and organic acid salts such as acetate, maleate, fumarate, citrate, malate, lactate, α-keto glutamate, gluconate, caprylate and the like.

Examples of the metal salt include alkali metal salts such as sodium salt, potassium salt and the like, alkaline earth metal salts such as magnesium salt, calcium salt and the like, aluminum salt, zinc salt and the like.

Examples of the ammonium salt include salts of ammonium, tetramethylammonium and the like.

Examples of the organic amine addition salt include salts of morpholine, piperidine and the like.

Examples of the amino acid addition salt include salts of glycine, phenylalanine, lysine, aspartic acid, glutamic acid and the like.

The composition of the present invention contains the above-mentioned fruit body of *Agaricus blazei* Murill or an extract of the fruit body, and an amino acid constituting the ornithine cycle or a salt thereof. The mixing weight ratio of the fruit body of *Agaricus blazei* Murill or an extract of the fruit body, and an amino acid constituting the ornithine cycle or a salt thereof is generally 1:10-100, preferably 1:20-80, more preferably 1:30-60, and the composition is preferably used as a pharmacological composition.

The composition of the present invention has the above-mentioned mixing weight ratio of the fruit body of *Agaricus blazei* Murill or an extract of the fruit body, and an amino acid constituting the ornithine cycle or a salt thereof, whereby the pharmacological activity expected by the administration of a fruit body of *Agaricus blazei* Murill or an extract of the fruit body, and an amino acid constituting the ornithine cycle or a salt thereof to human or non-human animals can be synergistically enhanced.

The pharmacological activity is not particularly limited as long as a fruit body of *Agaricus blazei* Murill or an extract of the fruit body, and an amino acid constituting the ornithine cycle or a salt thereof have. For example, enhancement and improvement of the liver, heart, stomach, intestines and the like, stabilization of blood pressure or blood glucose level, recovery of lumbago or neck stiffness, prevention of aging, improvement of immunity, antitumor action and the like can be mentioned.

The non-human animals include animals other than human such as mammals, birds, reptiles, amphibians, fish and the like, with preference given to mammals.

As the composition of the present invention, a fruit body of *Agaricus blazei* Murill or an extract of the fruit body, and an amino acid constituting the ornithine cycle or a salt thereof can be directly administered. Generally, the composition is desirably provided in the form of various preparations.

The preparation contains a fruit body of *Agaricus blazei* Murill or an extract of the fruit body, and an amino acid constituting the ornithine cycle or a salt thereof. Furthermore, it may contain any active ingredient such as vitamins, minerals and the like. The preparation is produced by mixing the active ingredient with one or more kinds of pharmacologically acceptable carriers, and according to any method well known in the technical field of preparation formulation.

The administration form of the preparation is, for example, oral administration or parenteral administration such as intravenous, peritoneal or subcutaneous administration and the like, with preference given to oral administration.

Examples of the dosage form for administration include oral agents such as tablet, powder, granule, pill, suspension, emulsion, infusion, decoction, capsule, syrup, liquid, elixir, extract, tincture, fluid extract and the like, and parenteral agents such as injection, drip infusion, cream, suppository and the like. It is preferably used as an oral preparation.

A liquid preparation suitable for oral administration, such as syrup, can be formulated as a preparation while adding water, saccharides such as saccharose, sorbitol, fructose and the like, glycols such as polyethylene glycol, propylene glycol and the like, oils such as sesame oil, olive oil, soybean oil and the like, antiseptics such as p-hydroxybenzoic acid esters and the like, preservatives such as p-oxybenzoic acid derivative such as methyl p-oxybenzoate and the like, sodium benzoate and the like, flavors such as strawberry flavor, peppermint and the like, and the like.

In addition, tablet, powder, granule and the like suitable for oral administration can be formulated as preparations while adding saccharides such as lactose, sucrose, glucose, saccharose, mannitol, sorbitol and the like, starches such as potato, wheat, corn and the like, inorganic materials such as calcium carbonate, calcium sulfate, sodium hydrogen carbonate, sodium chloride and the like, excipient such as plant powder and the like (e.g., crystalline cellulose, powdered *Glycyrrhiza uralensis, Gentiana lutea* powder and the like), disintegrants such as starch, agar, gelatin powder, crystalline cellulose, carmellose sodium, carmellose calcium, calcium carbonate, sodium hydrogen carbonate, sodium alginate and the like, lubricants such as magnesium stearate, talc, hydrogenation vegetable oil, macrogol, silicone oil and the like, binders such as polyvinyl alcohol, hydroxypropylcellulose, methylcellulose, ethylcellulose, carmellose, gelatin, starch paste and the like, surfactants such as fatty acid ester and the like, plasticizers such as glycerol and the like, and the like.

In addition, a preparation suitable for oral administration may contain additives generally used for food and drink, such as sweetener, coloring agent, preservative, thickening agent, antioxidant, color development agent, bleach, fungicide, gum base, bittering agent, enzyme, gloss, acidulant, seasoning, emulsifier, reinforcement, agent for production, flavor, condiment extract and the like.

A preparation suitable for oral administration may be used as it is or, for example, in the form of powder food, sheet food, bottled food, canned food, retort food, capsule food, tablet food, liquid food, drink and the like, or as food and drink such as health food, functional food, nutrition supplemental food, food for specified health uses and the like.

For example, an injection suitable for parenteral administration is a sterile aqueous agent containing a fruit body of *Agaricus blazei* Murill or an extract of the fruit body, and an amino acid constituting the ornithine cycle or a salt thereof, which is preferably isotonic with the blood of a recipient. For example, for injection, a solution for injection is prepared using a carrier which is a salt solution, a glucose solution or a mixture of a salt solution and a glucose solution, and the like.

The concentration of a fruit body of *Agaricus blazei* Murill or an extract of the fruit body, and an amino acid constituting the ornithine cycle or a salt thereof in the composition of the present invention is appropriately determined according to the kind of preparation, the effect expected to be afforded by the administration of the preparation and the like. It is generally 0.1-100 wt %, preferably 0.5-80 wt %, particularly preferably 1-70 wt %, based on a fruit body of *Agaricus blazei* Murill or an extract of the fruit body, and an amino acid constituting the ornithine cycle or a salt thereof.

When the composition of the present invention is administered to human, the dose and administration frequency vary depending on the administration form, and age, body weight and the like of the administration subject. The composition is administered once a day to several times a day such that generally 50 mg-30 g, preferably 100 mg-20 g, particularly preferably 200 mg-10 g, of a fruit body of *Agaricus blazei* Murill or an extract of the fruit body, and an amino acid constituting the ornithine cycle or a salt thereof will be administered to an adult per day.

While the dosing period is not particularly limited, it is generally 1 day-1 year, preferably 1 week-3 months.

When the composition of the present invention is administered to a non-human animal, the dose and administration frequency vary depending on the administration form, and age, kind and the like of the animal that receives administration. The composition is administered once a day to several times a day such that generally 1-600 mg, preferably 2-400 mg, particularly preferably 4-200 mg, of a fruit body of *Agaricus blazei* Murill or an extract of the fruit body, and an amino acid constituting the ornithine cycle or a salt thereof will be administered per 1 kg body weight per day.

While the dosing period is not particularly limited, it is generally 1 day-1 year, preferably 1 week-3 months.

An experimental example is shown below, wherein a synergistic effect of a combination of a freeze-dried product of *Agaricus blazei* Murill and arginine for an antitumor action, which is one of the pharmacological activities expected of a fruit body of *Agaricus blazei* Murill or an extract of the fruit body, and an amino acid constituting the ornithine cycle or a salt thereof, was examined. In the experimental example, a concentration at which *Agaricus blazei* Murill alone is ineffective was employed.

Experimental Example

BALB/cA Jcl-nu mice (male, 5-week-old) purchased from CLEA Japan, Inc. were preliminarily bred under constant conditions (temperature: 24±2° C., humidity: 60±5%, light-dark cycle: 12 hr) for 3 days or longer, and a tumor mass cut in a 2 mm square of human melanoma cell line SEKI (provided by National Cancer Center) was subcutaneously transplanted into the abdomen. From the day when the tumor was transplanted, the mice were allowed to freely ingest the composition produced in Example 1 or a control feed for 39 days. During this period, the body weight and tumor volume were measured twice a week. For the tumor volume, the major axis and the minor axis of the tumor were measured with a vernier caliper, and calculated by the following formula.

$$\text{tumor volume} = \tfrac{1}{2} \times \text{major axis} \times \text{minor axis} \times \text{minor axis}$$

The tumor weight was determined with the specific gravity of the tumor as 1 and the weight per 1 cm$^3$ tumor volume as 1 g.

The tumor weight at day 39 was shown in mean±standard error (g), and the statistical significance (p value) was determined by t-test.

The results are shown in Table 1.

TABLE 1

| | tumor weight (g) | n | p value |
|---|---|---|---|
| Example 1 (3% arginine + 0.1% Agaricus) | 0.25 ± 0.12 | 8 | 0.05> (relative to control 1) |
| | | | 0.05> (relative to control 2) |
| control 1 (3% arginine) | 0.59 ± 0.04 | 7 | 0.05< (relative to control 3) |
| control 2 (0.1% Agaricus) | 0.70 ± 0.14 | 7 | 0.05< (relative to control 3) |
| control 3 (CE-2) | 0.67 ± 0.21 | 8 | |

When the feed of control 1 was ingested, the tumor growth was likely to be suppressed but not significantly, as compared to ingestion of the feed of control 3. When the feed of control 2 was ingested, no tendency toward suppression of tumor growth was observed.

On the other hand, when the composition of Example 1 was ingested, tumor growth was remarkably suppressed, as compared to ingestion of the feeds of control 1 and control 2.

From the above, a synergistic effect was afforded by a combination of a fruit body of *Agaricus blazei* Murill or an extract of the fruit body, and an amino acid constituting the ornithine cycle or a salt thereof.

Examples of the present invention are shown below.

Example 1

Production of Composition Containing Arginine and Freeze-Dried Product of Agaricus An experimental animal powder feed CE-2 (manufactured by CLEA Japan, Inc., 0.969 kg) was homogeneously mixed with L-arginine (manufactured by KYOWA HAKKO KOGYO CO., LTD., 30 g) and agaricus freeze-dried product (agaricus granule SINWA, manufactured by Sinwa Pharmaceutical Co., Ltd., 1 g), whereby a composition containing 3.0 wt % L-arginine and 0.1 wt % agaricus freeze-dried product was produced.

Example 2

Production of Tablet Containing Arginine and Agaricus

A tablet containing arginine and agaricus is produced by a conventional method. To be precise, the following respective components are homogeneously mixed, and the mixture is tableted by a single punch tabletting machine to give a tablet having a diameter of 5 mm (weight 15 mg).

TABLE 2

| ingredients | amount |
|---|---|
| L-arginine | 9.5 g |
| agaricus extract 1 (Reference Example 1) | 0.5 g |
| lactose | 90.0 g |
| dried corn starch | 2.0 g |
| talc | 1.8 g |
| magnesium stearate | 0.2 g |

Example 3

Production of Granule Containing Arginine and Agaricus

The tablet obtained in Example 1 is pulverized, sized and sieved to give 20-50 mesh granules.

Example 4

Production of Drink Containing Ornithine and Agaricus

A drink containing ornithine and agaricus is produced by homogeneously dissolving the following respective ingredients by stirring, and adding purified water to the total amount of 1000 ml. The q.s. of flavor and dye in the following ingredients is an amount used for the production of general drinks, and q.s. of purified water is an amount necessary for making the total amount 1000 ml together with other ingredients.

TABLE 3

| ingredients | amount |
|---|---|
| L-ornithine | 4.8 g |
| Agaricus extract 2 (Reference Example 2) | 0.2 g |
| sodium benzoate | 1.0 g |
| fructose | 10.0 g |
| flavor | q.s. |
| dye | q.s. |
| purified water | q.s. |

Example 5

Production of Drink Containing Citrulline and Agaricus

A drink containing citrulline and agaricus is produced by homogeneously dissolving the following respective ingredients by stirring, and adding purified water to the total amount of 1000 ml. The q.s. of the following ingredients is as defined for Example 4.

TABLE 4

| ingredients | amount |
|---|---|
| L-citrulline | 4.8 g |
| Agaricus extract 2 (Reference Example 2) | 0.2 g |
| sodium benzoate | 1.0 g |
| fructose | 10.0 g |
| flavor | q.s. |
| dye | q.s. |
| purified water | q.s. |

Reference Example 1

Production of Agaricus Extract (1)

*Agaricus blazei* Murill (300 g, Kyowa Agaricus Blazei Murill) is added with distilled water (2 L) and the mixture was heated under reflux for 2 hr. This was separated into a filtrate (hot water extract) and a residue by filtration.

Distilled water (2 L) was added again to the residue, and the mixture was heated under reflux for 2 hr and subjected to hot water extraction to give a filtrate. The residue was subjected to similar hot water extraction again, and the filtrates were combined. The combined filtrate (hot water extract) was freeze-dried to give a dried substance (153 g). Distilled water (500 mL) was added to the dried substance (50 g) and the mixture was placed in a dialysis tube (Spectra/Por Membrane 50×31, 8 mm id×30 m, FE-0526-65). This was dialyzed against 3 L of distilled water for 12 hr. The external dialysis solution was freeze-dried to give a dried substance (27 g). The dried substance (3 g) was dissolved in 30 mL of distilled water and subjected to chromatography using TOYOPEARL HW40C (40 mm id×420 mm) (elution solvent: distilled water). A main elution chromatography fraction having a molecular weight of 100-2000 was obtained (agaricus extract 1).

Reference Example 2

Production of Agaricus Extract (2)

A hot water extraction similar to that in Reference Example 1 was performed to give a combined filtrate (hot water extract, 6 L). The filtrate was concentrated under reduced pressure to 1 L. Ethanol (1 L) was added and the mixture was centrifuged to give a precipitate and a supernatant fluid. Ethanol (3 L) was further added to the supernatant fluid and the mixture was centrifuged. The obtained precipitate was dissolved in distilled water and dialyzed. The obtained external dialysis solution was freeze-dried to give a powder (agaricus extract 2).

INDUSTRIAL APPLICABILITY

The present invention provides a composition comprising a fruit body of *Agaricus blazei* Murill or an extract of the fruit body, and an amino acid constituting the ornithine cycle or a salt thereof, which exhibits a superior pharmacological activity.

The invention claimed is:

1. A composition comprising (a) a fruit body of *Agaricus blazei* Murill or an extract of the fruit body, and (b) 20-80 parts by total weight of one or more of arginine, ornithine, citrulline, and salts thereof per 1 part by weight of the fruit body or the extract, wherein component (a) and component (b) are 0.5-80% by weight of the composition.

2. The composition of claim 1, wherein component (a) and component (b) are 1.0-70% by weight of the composition.

3. The composition of claim 1, wherein component (b) is arginine.

4. A composition comprising (a) a fruit body of *Agaricus blazei* Murill or an extract of the fruit body, and (b) 30-60 parts by total weight of one or more of arginine, ornithine, citrulline, and salts thereof per 1 part by weight of the fruit body or the extract, wherein component (a) and component (b) are 0.5-80% by weight of the composition.

5. The composition of claim 4, wherein component (a) and component (b) are 1.0-70% by weight of the composition.

6. The composition of claim 4, wherein component (b) is arginine.

* * * * *